United States Patent [19]

Kosak

[11] Patent Number: 5,449,780
[45] Date of Patent: Sep. 12, 1995

[54] PROCESS FOR THE PREPARATION OF 1,3- AND 1,5-DIALKYLPIPERIDONE-2

[75] Inventor: John R. Kosak, Greenville, Del.

[73] Assignee: E. I. Du Pont de Nemours and Company, Wilmington, Del.

[21] Appl. No.: 208,180

[22] Filed: Mar. 10, 1994

[51] Int. Cl.$^6$ .......................................... C07D 211/76
[52] U.S. Cl. ................................................... 546/243
[58] Field of Search ............................... 546/243, 242

[56] References Cited

U.S. PATENT DOCUMENTS

| | | | |
|---|---|---|---|
| 3,666,766 | 5/1972 | Pedigo et al. | 546/252 |
| 4,152,331 | 5/1979 | Meijer et al. | 546/252 |
| 4,876,348 | 10/1989 | DiCosimo et al. | 546/252 |

Primary Examiner—C. Warren Ivy
Assistant Examiner—Raymond Covington

[57] ABSTRACT

A process for the manufacture of 1,3- and 1,5-dialkyl-piperidone-2 by reacting 2-methylglutaronitrile with a primary alkylamine in the presence of hydrogen, water, and a hydrogenation catalyst.

3 Claims, No Drawings

PROCESS FOR THE PREPARATION OF 1,3- AND 1,5-DIALKYLPIPERIDONE-2

FIELD OF THE INVENTION

This invention relates the preparation of 1,3- and 1,5-dialkylpiperidone-2 from 2-methylglutaronitrile.

BACKGROUND OF THE INVENTION 2-methylglutaronitrile is a by-product in the hydrocyanation of butadiene to form adiponitrile. (Adiponitrile is hydrogenated to form hexamethylene diamine; which is one of the components in the manufacture of nylon 6,6.) 2-methylglutaronitrile does not have many industrial uses, and the conversion of 2-methylglutaronitrile to compounds having other properties and uses is an object of this invention. It is known to convert succinonitrile to N-substituted pyrrolidones by reacting it with hydrogen in the presence of a primary amine, and then hydrolyzing the reaction product to form the pyrrolidone: see U.S. Pat. No. 4,152,331.

SUMMARY OF THE INVENTION

The present invention is a process for the production of 1,3-dialkylpiperidone-2 and 1,5-dialkylpiperidone-2 which comprises forming a reaction mixture of methylglutaronitrile, an alkyl primary amine having 1 to 18 carbon atoms, water, hydrogen, and a hydrogenation catalyst, heating the reaction mixture to a temperature above about 150 degrees C at a pressure above about 150 p.s.i.g, and recovering 1,3-dialkylpiperidone-2 and 1,5-dialkylpiperidone-2. Preferred hydrogenation catalysts are selected from the class consisting of Group 8 metals, nickel and cobalt, and the most preferred catalyst contains palladium or platinum or both palladium and platinum. The most preferred primary amine is methylamine. The most preferred products are 1,3-dimethylpiperidone-2, and 1,5-dimethylpiperidone-2. The present invention is also the compound: 1,5-dimethylpiperidone-2.

1,3- and 1,5-dialkylpiperidone-2 is useful as a solvent, and can be directly substituted for N-methylpyrrolidone in many situations where it is used as a solvent.

DETAILED DESCRIPTION

Conventional commercial hydrogenation catalysts are useful in the process of the invention. Such catalysts are usually inert substrates such as carbon, alumina, strontium carbonate, silica and kieselguhr, having the metallic catalyst component dispersed on the surface. The amount of catalyst employed will vary with the particular catalytic metal employed, the concentration of the metal on the substrate, the type of reactor, and the reaction conditions.

It is preferred to carry out the process at temperatures above about 180 degrees and at pressures above about 1500 p.s.i.

Hydrogen and the primary alkylamine should each be present in the reactor in at least a stoichiometric amounts.

EXAMPLE 1

Into a 300 ml Hastelloy C autoclave there was charged 92 g of 2-methylglutaronitrile, 75 ml of 40% methylamine solution and 1.5 g of a 5% Pd on Strontium carbonate catalyst. After evacuation and purging twice with nitrogen the autoclave was purged with hydrogen and then pressured to 500 p.s.i.g with hydrogen. The mass was then heated to 150 C., pressured to 2000 p.s.i.g with hydrogen and the agitator was turned on. The reaction was run for 6 hours. GC analysis of the reaction mass showed the presence of 45.3 % of a mixture of 1,3- and 1,5-dimethylpiperidone-2.

EXAMPLE 2

Same as 1 above except the catalyst is 1.5 g of 4.5% Pd and 0.5% Pt on carbon and the temperature is 200 C. The GC yield of dimethylpiperidones-2 is 51.7%.

What is claimed is:

1. A process for the production of 1,3-dialkylpiperidone-2 and 1,5-dialkylpiperidone-2 which comprises forming a reaction mixture of methylglutaronitrile, an alkyl primary amine having 1 to 18 carbon atoms, water, hydrogen, and hydrogenation catalyst, selected from the group consisting of (a) palladium on strontium carbonate, and (b) palladium and platinum on carbon, heating the reaction mixture to a temperature above about 150 degrees C at a pressure above about 150 p.s.i.g., and recovering 1,3-dialkylpiperidone-2 and 1,5-dialkylpiperidone-2.

2. The process of claim 1 in which the alkyl primary amine is methylamine, and in which the products are 1,3-dimethylpiperidone-2, and 1,5-dimethylpiperidone-2.

3. 1,5-dimethylpiperidone-2.

* * * * *